(12) United States Patent
Eger

(10) Patent No.: US 8,306,599 B2
(45) Date of Patent: Nov. 6, 2012

(54) PROCESS AND DEVICE FOR MONITORING THE STATUS OF THE BODY FLUIDS OF A PERSON

(75) Inventor: Marcus Eger, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1127 days.

(21) Appl. No.: 12/036,374

(22) Filed: Feb. 25, 2008

(65) Prior Publication Data

US 2008/0269587 A1    Oct. 30, 2008

(30) Foreign Application Priority Data

Apr. 24, 2007   (DE) .................. 10 2007 019 210

(51) Int. Cl.
A61B 5/00   (2006.01)
(52) U.S. Cl. ............ 600/388; 600/301; 600/307; 2/455; 2/456; 2/463; 2/1
(58) Field of Classification Search .......... 2/1, 455–458, 2/2.11, 2.14, 2.15, 6.6–6.8, 7, 8.1–8.8, 900–920; 600/306, 307, 344, 346, 389, 393, 412, 419, 600/549; 128/200.24, 200.27, 200.28, 201.13, 128/201.28, 201.29, 202.11–202.12, 202.19, 128/204.17, 204.18, 204.29, 205.24
See application file for complete search history.

(56) References Cited

U.S. PATENT DOCUMENTS

| | | | | |
|---|---|---|---|---|
| 2,693,088 A * | 11/1954 | Green | .............................. | 62/172 |
| 3,736,764 A * | 6/1973 | Chambers et al. | ................ | 62/89 |
| 4,546,778 A * | 10/1985 | Sullivan | ........................ | 600/531 |
| 5,421,326 A * | 6/1995 | Rankin et al. | ............ | 128/201.19 |
| 5,438,707 A * | 8/1995 | Horn | .................................. | 2/457 |
| 5,564,124 A | 10/1996 | Elsherif et al. | | |
| 5,774,902 A | 7/1998 | Gehse | | |
| 5,970,519 A * | 10/1999 | Weber | ................. | 2/81 |
| 6,209,144 B1 * | 4/2001 | Carter | ................ | 2/458 |

(Continued)

FOREIGN PATENT DOCUMENTS

DE    195 47 795 C2   6/1997

(Continued)

OTHER PUBLICATIONS

Recktenwal, G. "Volumetric Flow Rate Measurement", Portland State University, Department of Mechanical Engineering, 2006, p. 1-16.*

(Continued)

Primary Examiner — Gregory A. Morse
Assistant Examiner — Marie Archer
(74) Attorney, Agent, or Firm — McGlew and Tuttle, P.C.

(57) ABSTRACT

A process and a device are provided for monitoring the status of the body fluids of a person. The device includes a piece of clothing with ventilating ducts, a first temperature sensor (6) and a first moisture sensor (11) for measuring the inlet flow (7) into the piece of clothing and a second temperature sensor (17) and a second moisture sensor (12) for measuring the outlet flow (10) from the piece of clothing. A pressure sensor (13) is provided sensing pressure in the inlet flow. A fan (5) or a compressed-air source is provided for transporting the cooling air into the piece of clothing. A measuring and analyzing unit (14) is connected to the sensors and the fan (5) or the compressed-air source.

19 Claims, 1 Drawing Sheet

U.S. PATENT DOCUMENTS

| | | | |
|---|---|---|---|
| 6,209,194 B1 * | 4/2001 | Kang et al. | 29/739 |
| 6,581,677 B2 * | 6/2003 | Dukes-Dobos et al. | 165/11.1 |
| 2001/0003907 A1 * | 6/2001 | Siman-Tov et al. | 62/259.3 |
| 2004/0083526 A1 | 5/2004 | Ichigaya | |
| 2005/0197684 A1 | 9/2005 | Koch | |
| 2006/0191270 A1 | 8/2006 | Warren | |
| 2007/0000008 A1 * | 1/2007 | Sawicki et al. | 2/69 |
| 2007/0018836 A1 * | 1/2007 | Richardson | 340/622 |
| 2007/0289050 A1 * | 12/2007 | Nocente et al. | 2/458 |

FOREIGN PATENT DOCUMENTS

| | | |
|---|---|---|
| DE | 102004011139 | 10/2005 |
| EP | 0490347 A1 | 6/1992 |
| FR | 2783138 A1 | 3/2000 |
| WO | WO 2005/034661 A1 | 4/2005 |
| WO | WO 2007/005391 A2 | 1/2007 |

OTHER PUBLICATIONS

McLellan, T. M., "The efficacy of an air-cooling vest to reduce thermal strain for light armor vehicle personnel", Defense R&D Canada—Toronto Technical Report, DRDC Toronto TR 2007-002, Jan. 2007, p. 1-34.*

Xhengxiang, P. "A dynamic model of the human/cooling system/cooling/environment system", PhD dissertation submitted in the Department of Mechanical Engineering at the University of central Florida, Spring 2005, p. 1-143.*

Wagner, et al in "Standardisation of the measurement of lung volumes", Eur Respir J 2005; 26: 511-522.).*

NPL_airflow_meas_ref.pdf, p. 1.*

Tomizuka, M et al "Soldier protective clothing and equipment", Committee on Full-System Testing and Evaluation of Personal Protection, National Academies of Equipment Ensembles in Simulated Chemical-Warfare Environments, 2008, p. 1-171.*

Shaw, G. A. et al, "Warfighter Physiological and Environmental Monitoring: A Study for the U.S. Army Research Institute in Environmental Medicine and the Soldier Systems Center", Lincoln Laboratories, MIT, 2004, p. 1-141.*

* cited by examiner

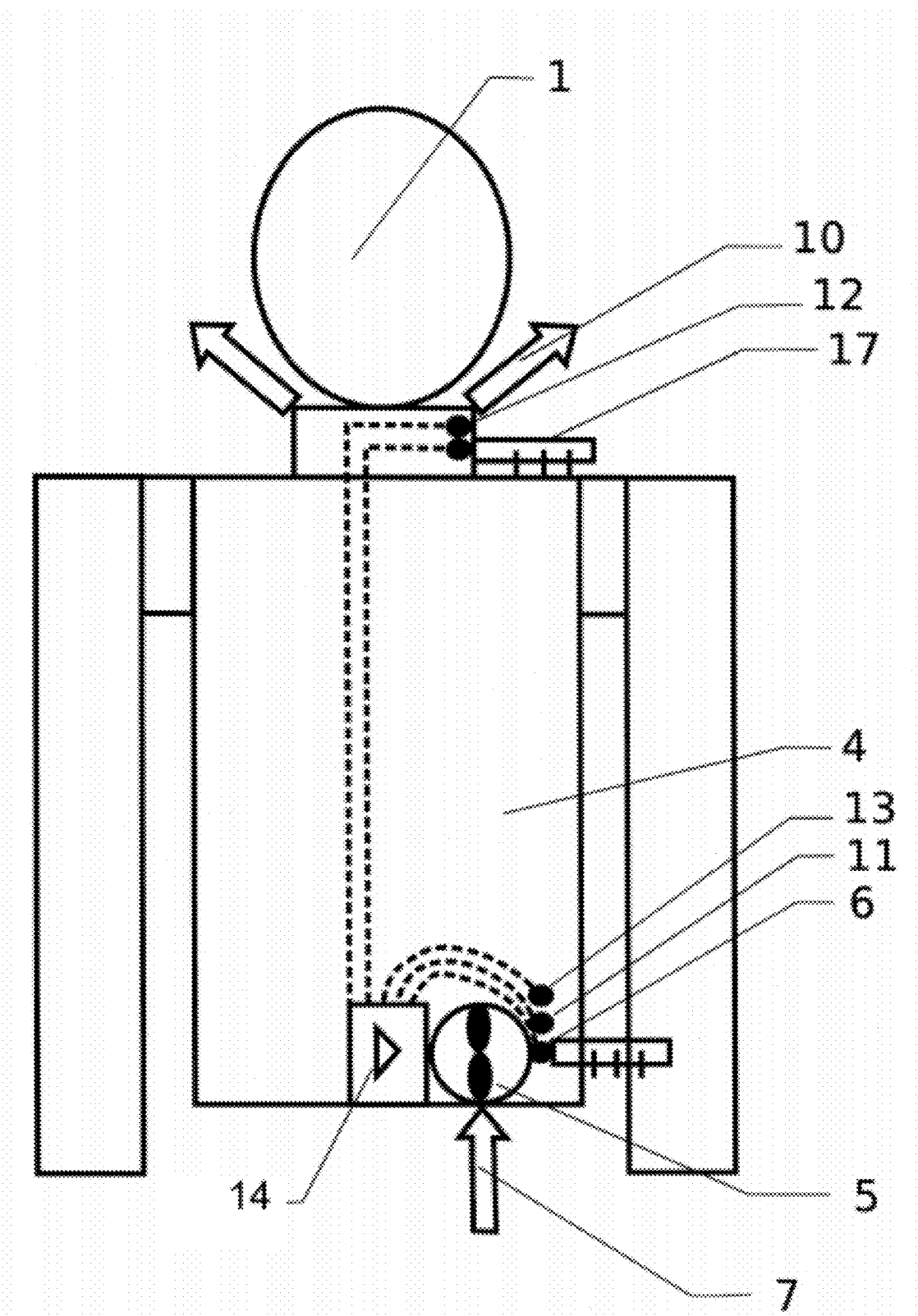

PROCESS AND DEVICE FOR MONITORING THE STATUS OF THE BODY FLUIDS OF A PERSON

CROSS REFERENCE TO RELATED APPLICATIONS

This application claims the benefit of priority under 35 U.S.C. §119 of German Patent Application 10 2007 019 210.1 filed Apr. 24, 2007, the entire contents of which are incorporated herein by reference.

FIELD OF THE INVENTION

The present invention pertains to a process for monitoring the status of the body fluids or the dehydration of a person and to a device for carrying out the process.

BACKGROUND OF THE INVENTION

The monitoring and maintenance of a physiologically suitable body climate and here especially of the status of the body fluids is very important for well-being especially in persons who are subject to physical stress such as, for example, firefighters. During missions, such persons wear protective clothing or clothing parts that offer protection against the environment and may be fire-resistant.

Such special clothing has, for example, according to DE 195 47 795 C2 (corresponding to U.S. Pat. No. 5,774,902), an outer protective layer, which offers protection against undesired effects from the outside, an inner layer permeable to moisture and/or vapor and a distance-maintaining spacer layer, which is permeable to fluids, is arranged between the outer protective layer and the inner layer and can be climatized by introducing a fluid.

DE 10 2004 011139 A1 (corresponding to U.S. application Ser. No. 10/979,713) discloses a device for body climate control with:
a piece of clothing with ventilating ducts, which are connected at their inlet and outlet to the environment, with at least one temperature sensor, which detects the body temperature of the wearer of the piece of clothing, with a fan, which admits ambient air into the ventilating ducts, and with a measuring and analyzing unit, which is connected to the at least one temperature sensor and the fan.

Besides the risk of thermal and physical overload, members of mission crews performing hard physical work, especially firefighters, run the risk of dehydration. An aggravating circumstance is that the loss of water is manifested in a drop in performance capacity and increase in the body core temperature. A fatal circulatory collapse may develop due to these causes, especially in case of long mission times.

Attempts at describing the actual moisture balance under mission conditions by means of physiological models have not been successful and are not suitable for the conditions of practical use.

SUMMARY OF THE INVENTION

The object of the present invention is therefore to provide a process for monitoring the status of the body fluids or the dehydration of a person and to provide a device for carrying out the process.

According to one aspect of the invention, a process is provided for monitoring the status of body fluids of a person. The process comprises providing a person with a piece of clothing with ventilating ducts. A first temperature sensor and a first moisture sensor are positioned for measuring inlet flow into the piece of clothing with the first temperature sensor and with the first moisture sensor. A second temperature sensor and a second moisture sensor are positioned for measuring outlet flow from the piece of clothing with the second temperature sensor and with the second moisture sensor. A pressure sensor is provided in the inlet flow. A fan or a compressed-air source is provided for the transport of cooling air into the piece of clothing and to provide the inlet flow and the outlet flow. A measuring and analyzing unit is connected to the sensors and to the fan or compressed-air source. The fan or the compressed-air source is activated and measuring pressure established at the air inlet in the inlet flow is measured with the pressure sensor in the inlet flow. Gas volume flow is determined. Moisture content of the gas volume flow in the inlet flow is measured. The moisture content of the gas volume flow in the outlet flow is measured. The moisture currently being fed and the moisture currently being removed from the gas volume flow and the measured moisture content is determined. A loss of moisture by the person from the determined time integral of the difference between the moisture fed in and the moisture removed or from the difference between the time integrals of the moisture fed in and the moisture removed is determined.

The loss of moisture may be compared to a limit value and an alarm signal may be sent by the measuring and analyzing unit when the limit value is exceeded.

The moisture content may be determined either by direct absolute measurements or calculated via a relative moisture measurement with complementary temperature measurement in the inlet flow and in the outlet flow. The gas volume flow may be determined on the basis of the current speed of the fan from a characteristic speed-dependent volume flow curve.

The determination of the loss of moisture may further include determining moisture gained or released by breathing including measuring the respiratory volume of the person to determine moisture fed in and the absolute moisture content in the breathing air breathed in.

According to another aspect of the invention, a device is provided for monitoring the status of the body fluids of a person (clothing wearer). The device includes a piece of clothing with ventilating ducts, a first temperature sensor and a first moisture sensor for measuring inlet flow into the piece of clothing and a second temperature sensor and a second moisture sensor for measuring outlet flow from the piece of clothing. A pressure sensor is provided for detecting pressure of the inlet flow. A fan or a compressed-air source is provided for transporting the cooling air into the piece of clothing for the inlet flow and the outlet flow. A measuring and analyzing unit is connected to the first temperature sensor, connected to the first moisture sensor, connected to the second temperature sensor and connected to the second moisture sensor and connected to the fan or the compressed-air source.

The measuring and analyzing unit may advantageously determine gas volume flow and determine, from gas volume flow and from a measured moisture content, moisture currently being fed and moisture currently being removed from the gas volume flow and the measured moisture content. A loss of moisture, by the person, may then be determined from the determined time integral of the difference between the moisture fed in and the moisture removed or from the difference between the time integrals of the moisture fed in and the moisture removed.

The fan may be a radial compressor. The moisture sensors may be capacitive or resistive sensors. The moisture sensors may be Surface Acoustic Wave (SAW) and/or piezo resonance sensors. The piece of clothing with ventilating ducts may advantageously comprise protective clothing.

A device for carrying out the process for monitoring the status of the body fluids of a person will be explained below on the basis of the sole figure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWINGS

In the drawings:

The only FIGURE is a schematic view of a device for monitoring the status of the body fluids of a person according to the invention.

DESCRIPTION OF THE PREFERRED EMBODIMENT

Referring to the drawings in particular, the device according to the invention is schematically shown in the figure as including a cooling clothing or a piece of clothing of a wearer 1 in the form of a vest 4 with inherent ventilating ducts, not shown specifically, with a fan 5 with an inlet flow 7 for ambient air, with a first temperature sensor 6 and with a first moisture sensor 11 for measuring the inlet flow 7 as well as with a second temperature sensor 17 and a second moisture sensor 12 for measuring the outlet flow 10. Furthermore, a pressure sensor 13 is located in the inlet area at the fan 5 for detecting the pressure relative to the environment at the air inlet. As an alternative, two pressure sensors may be used to measure the absolute pressure at the air inlet and in the environment, so that the pressure difference needed for the analysis is determined from it. As an alternative, it would be possible to determine the total flow of the cooling medium or of the air by means of a corresponding gas flow sensor system, which is known per se, without measuring the pressure, but this is expensive.

All sensors as well as the fan 5 are connected to the measuring and analyzing unit 14.

In a piece of clothing cooled actively by convection, the cooling of the wearer 1 takes place by the improved evaporation of the sweat by means of the cooling medium used, i.e., especially sufficiently cool and dry air, which is drawn in, in general, from the environment or is fed, as an alternative, as compressed air from a compressed-air bottle or compressed-air source. The air or the cooling medium used is pumped into the piece of clothing or into the cooling clothing, it takes up the sweat there and is then drawn off as a outlet flow 10. The piece of clothing has a dense outer shell and therefore prevents leaks and unnecessarily strong air or cooling medium flows. The side of the piece of clothing facing the body surface of the wearer 1 is open for diffusion in order to achieve the greatest possible exchange of moisture. A space, through which cooling medium flows and which is embodied, for example, by a knitted textile spacer product or by ventilating ducts, is located in-between. Since the outer shell of the cooling clothing is airtight, the total amount of moisture is transported to the outside and released at the outlet by the outlet flow 10. The loss of liquid of the wearer 1 is determined by means of the measured inlet and outlet temperatures T1 and T2 as well as the measured relative inlet and outlet moisture contents F1 and F2 and from the total flow of the cooling medium.

As an alternative, the absolute moisture contents can be measured and used to determine the liquid loss of the wearer 1, so that the temperatures T1 and T2 and hence the corresponding temperature sensors 6, 17 are not necessary in this case and are eliminated. The total flow is known either from a preset setting of the fan 5 or the compressed air fed in or it can be calculated especially from the pressure-vs.-flow characteristic of the fan 5 by the measuring and analyzing unit 14.

The pressure must be known for this or it is measured by means of the pressure sensor 13 in the inlet.

When the expired air is likewise removed via the outlet located in the piece of clothing and the respiratory minute volume is measured, the amount of liquid released via the expired air can also be taken into account when determining the total loss of liquid by the measuring and analyzing unit 14. The liquid released by urination and the liquid intake by drinking have, of course, to be taken into account in the overall balance for the wearer 1. When the total loss of liquid has exceeded a certain threshold value, an alarm can be triggered or the person participating in the mission, i.e., the wearer 1, is asked to withdraw from the site or area of the mission.

The process of monitoring the status of the body fluid comprises the following steps:
1. The fan 5 or the compressed air fed in is switched on.
2. The pressure becoming established at the air inlet relative to the environment is measured.
3. The current gas volume flow of the air flowing into the piece of clothing, which is determined by means of the measured pressure, is measured.
4. The moisture currently being fed is determined from the gas volume flow and the measured absolute moisture content in the air inlet, or, as an alternative, from the measured relative moisture content and the temperature.
5. The moisture currently being removed is determined from the gas volume flow and the measured absolute moisture in the air outlet or, as an alternative, from the measured relative moisture and the temperature.
6. The loss of moisture is determined from the time integral of the difference between the moisture fed in and removed or, as an alternative, from the difference between the time integrals of the moisture fed in and removed.
7. If the loss of moisture exceeds a preset limit value, the measuring and analyzing unit 14 sends an alarm signal, which is passed on either to a mission center and/or is outputted directly in the area of perception of the wearer 1 as a visual and/or audio display.

The piece of clothing or the cooling clothing is optionally designed such that the air breathed out by the wearer 1 is likewise determined, for example, it is breathed into the cooling clothing, so that higher accuracy of the determined moisture balance is possible. In addition, it would be necessary in this case to use a breath flow sensor for determining the respiratory minute volume.

The following supplementary or modified process steps should be provided for now:
a) The respiratory minute volume of the wearer 1 is additionally measured.
b) The moisture fed in additionally is determined from the respiratory minute volume and the absolute moisture content in the breathing air breathed in.
c) The total amount of moisture currently being fed to the wearer 1 is determined from the sum of the moisture fed additionally and the moisture determined from the gas flow and the absolute moisture content at the air inlet.
d) The total amount of moisture currently being removed is determined from the sum of the respiratory minute volume and the cooling gas flow as well as the absolute moisture content at the air outlet.
e) The loss of moisture is determined from the time integral of the difference between the total amount of moisture fed in and the total amount of moisture removed or, as an alternative, from the difference between the time integrals of the total amount of moisture fed in and the total amount of moisture removed.

The moisture sensors 11, 12 of the device are designed, in general, as relative moisture sensors and are preferably capacitive or resistive or semiconductor sensors. SAW (Surface Acoustic Wave) sensors or piezo resonance sensors may also be considered. As an alternative, LiCl dew point hygrometers, dew level hygrometers, and electrolysis hygrometers are considered, in principle, as moisture sensors measuring the absolute moisture directly.

While a specific embodiment of the invention has been shown and described in detail to illustrate the application of the principles of the invention, it will be understood that the invention may be embodied otherwise without departing from such principles.

What is claimed is:

1. A process for monitoring the status of body fluids of a person, the process comprising the steps of:
    providing a person with a piece of clothing with ventilating ducts;
    providing a first temperature sensor and a first moisture sensor positioned for measuring inlet flow into the piece of clothing with the first temperature sensor and with the first moisture sensor;
    providing a second temperature sensor and a second moisture sensor positioned for measuring outlet flow from the piece of clothing with the second temperature sensor and with the second moisture sensor;
    providing a pressure sensor in the inlet flow;
    providing a fan or a compressed-air source providing cooling air into the piece of clothing and to provide the inlet flow and the outlet flow;
    providing a measuring and analyzing unit connected to said first temperature sensor, said first moisture sensor, said second temperature sensor, said second moisture sensor, said pressure sensor and the fan or the compressed-air source;
    activating the fan or the compressed-air source;
    measuring pressure established at the air inlet in the inlet flow with the pressure sensor in the inlet flow;
    determining gas volume flow based on said measured pressure;
    measuring an inlet flow moisture content of the gas volume flow in the inlet flow with said first moisture sensor;
    measuring an outlet flow moisture content of the gas volume flow in the outlet flow with said second moisture sensor;
    determining moisture currently being fed and moisture currently being removed from the gas volume flow based on at least said gas volume flow, said inlet flow measured moisture content and said outlet flow moisture content;
    determining a loss of moisture by the person from a determined time integral of a difference between the moisture fed in and the moisture removed or from the difference between time integrals of the moisture fed in and the moisture removed, wherein said loss of moisture is compared to a limit value and an alarm signal is sent by the measuring and analyzing unit when the limit value is exceeded.

2. A process in accordance with claim 1, wherein the moisture content is determined either by direct absolute measurements or calculated via a relative moisture measurement with complementary temperature measurement in the inlet flow with said first temperature sensor and in the outlet flow with said second temperature sensor.

3. A process in accordance with claim 1, wherein the gas volume flow is determined on the basis of the current speed of the fan from a characteristic speed-dependent volume flow curve 4. A process in accordance with claim 1, wherein determining a loss of moisture further includes determining moisture gained or released by breathing including measuring a respiratory volume of the person to determine moisture fed in and an absolute moisture content in the breathing air breathed in.

5. A process in accordance with claim 1, wherein said first temperature sensor, said first moisture sensor, said second temperature sensor, said measuring and analyzing unit, said second moisture sensor, said fan and said pressure sensor are connected to said clothing, said pressure sensor being arranged at or adjacent to said fan, wherein said first temperature sensor measures an inlet temperature and said second temperature sensor measures an outlet temperature, wherein said inlet temperature and said second temperature sensor are used in said step of determining said moisture currently being fed and said moisture currently being removed from the gas volume flow, said piece of clothing defining a flow inlet area, said cooling fluid entering said piece of clothing at said flow inlet area, said piece of clothing defining a flow outlet area, said flow outlet exiting said piece of clothing at said flow outlet area, said flow inlet area and said flow outlet area defining at least a cooling fluid flow path in said piece of clothing, said cooling fluid passing through said cooling fluid flow path.

6. A device for monitoring the status of the body fluids of a person, the device comprising:
    a piece of clothing with ventilating ducts;
    a first temperature sensor and a first moisture sensor for measuring inlet flow into said piece of clothing;
    a second temperature sensor and a second moisture sensor for measuring outlet flow from the piece of clothing;
    a pressure sensor detecting pressure of the inlet flow;
    a fan or a compressed-air source transporting cooling air into the piece of clothing for said inlet flow and said outlet flow;
    a measuring and analyzing unit connected to said first temperature sensor, connected to said first moisture sensor, connected to said second temperature sensor and connected to said second moisture sensor and connected to said fan or the compressed-air source.

7. A device in accordance with claim 6, wherein said fan is a radial compressor, said measuring analyzing unit determining a loss of moisture based on output from said first temperature, said first moisture sensor, said second temperature sensor and said second moisture sensor, wherein said loss of moisture is compared to a limit value and an alarm signal is sent by the measuring and analyzing unit when the limit value is exceeded.

8. A device in accordance with claim 6, wherein said moisture sensors are capacitive or resistive sensors.

9. A device in accordance with claim 6, wherein said moisture sensors are Surface Acoustic Wave (SAW) or piezo resonance sensors.

10. A device in accordance with claim 6, wherein said piece of clothing with ventilating ducts comprises protective clothing.

11. A device in accordance with claim 6, wherein an inlet measured moisture content is measured via said first moisture sensor and an outlet measured moisture content is measured via said second moisture sensor, said first temperature sensor measuring an inlet temperature and said second temperature sensor measuring an outlet temperature, said measuring and analyzing unit determining a gas volume flow based on said detected pressure of said inlet flow and said measuring and analyzing unit determining moisture currently being fed and moisture currently being removed from the gas volume flow based on said gas volume flow, said inlet temperature, said outlet temperature, said inlet measured moisture content and said outlet measured moisture content and said measuring and analyzing unit determining a loss of moisture by the person from the determined time integral of a difference between the moisture fed in and the moisture removed or from the difference between time integrals of the moisture fed in and the moisture removed.

12. A device in accordance with claim 11, wherein said first temperature sensor, said first moisture sensor, said second temperature sensor, said measuring and analyzing unit, said second moisture sensor, said fan and said pressure sensor are connected to said clothing, said pressure sensor being arranged at or adjacent to said fan, said piece of clothing defining a flow inlet area, said cooling fluid entering said piece of clothing at said flow inlet area, said piece of clothing defining a flow outlet area, said flow outlet exiting said piece of clothing at said flow outlet area, said flow inlet area and said flow outlet area defining at least a cooling fluid flow path in said piece of clothing, said cooling fluid passing through said cooling fluid flow path.

13. A device for monitoring the status of the body fluids of a person, the device comprising:
 a piece of clothing with ventilating ducts;
 a first temperature sensor and a first moisture sensor for measuring inlet flow into said piece of clothing;
 a second temperature sensor and a second moisture sensor for measuring outlet flow from the piece of clothing;
 a pressure sensor detecting pressure of the inlet flow;
 a fan or a compressed-air source providing cooling air into the piece of clothing for said inlet flow and said outlet flow;
 a measuring and analyzing unit connected to said first temperature sensor, connected to said first moisture sensor, connected to said second temperature sensor, connected to said second moisture sensor, connected to said fan or the compressed-air source and connected to said pressure sensor, said measuring and analyzing unit determining gas volume flow based on said detected pressure of said inlet flow and determining, from said gas volume flow and from a measured moisture content, moisture currently being fed and moisture currently being removed based on the gas volume flow and the measured moisture content and determining a loss of moisture by the person from a determined time integral of a difference between the moisture fed in and the moisture removed or from a difference between time integrals of the moisture fed in and the moisture removed.

14. A device in accordance with claim 13, wherein said fan is a radial compressor, wherein said loss of moisture is compared to a limit value and an alarm signal is sent by the measuring and analyzing unit when the limit value is exceeded.

15. A device in accordance with claim 13, wherein said moisture sensors are capacitive or resistive sensors.

16. A device in accordance with claim 13, wherein said moisture sensors are at least one of Surface Acoustic Wave (SAW) and piezo resonance sensors.

17. A device in accordance with claim 13, wherein determining a loss of moisture further includes determining moisture gained or released by breathing including measuring the respiratory volume of the person to determine moisture fed in and the absolute moisture content in the breathing air breathed in.

18. A device in accordance with claim 13, wherein said piece of clothing with ventilating ducts comprises protective clothing.

19. A device in accordance with claim 13, wherein said first temperature sensor, said first moisture sensor, said second temperature sensor, said measuring and analyzing unit, said second moisture sensor, said fan and said pressure sensor are connected to said clothing, said pressure sensor being arranged at or adjacent to said fan, wherein said first temperature sensor measures an inlet temperature and said second temperature sensor measures an outlet temperature, wherein measuring and analyzing unit determines said moisture currently being fed and said moisture currently being removed from the gas volume flow based on said inlet temperature and said second temperature sensor, said piece of clothing defining a flow inlet area, said cooling fluid entering said piece of clothing at said flow inlet area, said piece of clothing defining a flow outlet area, said flow outlet exiting said piece of clothing at said flow outlet area, said flow inlet area and said flow outlet area defining at least a cooling fluid flow path in said piece of clothing, said cooling fluid passing through said cooling fluid flow path.

* * * * *